United States Patent

Lazzara et al.

[11] Patent Number: 5,364,268
[45] Date of Patent: Nov. 15, 1994

[54] METHOD FOR INSTALLING A DENTAL IMPLANT FIXTURE IN CORTICAL BONE

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 845,138

[22] Filed: Mar. 3, 1992

[51] Int. Cl.⁵ .............................. A61C 8/00
[52] U.S. Cl. ............................ 433/173
[58] Field of Search ............. 433/173, 174, 175, 176

[56] References Cited

U.S. PATENT DOCUMENTS

| | | | |
|---|---|---|---|
| 4,424,037 | 1/1984 | Ogino et al. | 433/173 |
| 4,668,191 | 5/1987 | Plischka | 433/174 |
| 4,863,383 | 9/1989 | Grafelmann | 433/174 |
| 4,934,935 | 6/1990 | Edwards | 433/173 |
| 5,135,394 | 8/1992 | Hakamatsuka et al. | 433/173 |

*Primary Examiner*—John J. Wilson
*Attorney, Agent, or Firm*—Alfred H. Rosen

[57] ABSTRACT

A dental implant fixture intended for installation in maxillary and mandibular posterior regions where bone is cancellous internally ant cortical externally characterized by labial and lingual cortical plates bounding a relatively large body of cancellous bone. The body of the implant fixture has a width dimension that is substantially the same as the distance between the labial and lingual cortical plates in the site of installation When installed in that site the implant fixture makes bone-to-implant contact with both of the plates simultaneously The length of this implant fixture is limited so that when installed it does not make contact with the mandibular canal or the sinus cavities.

6 Claims, 1 Drawing Sheet

METHOD FOR INSTALLING A DENTAL IMPLANT FIXTURE IN CORTICAL BONE

BACKGROUND OF THE INVENTION

This invention relates to dental implants, particularly to implants intended for installation in the maxillary and mandibular posterior regions where bone is cancellous internally and cortical externally.

As it has developed to the present time, the technology of dental implants preferentially employs cylindrical implants, some externally threaded, and some not threaded, but all being much longer than they are wide with the ratio of length to width being about 1.8 to 5.3, for example. This may be due primarily to the fact that early successes were experienced with installation in the anterior area of dental arches. Thus, dental implants commonly available at the present time have lengths ranging up to about 20 mm and widths up to about 4 mm. Predictability of this type of installtion in the anterior area of dental arches is now so good that the use of dental implants has entered the armamentarium of oral surgeons, prosthodontists and periodontists in the treatment of fully and partially edentulous patients. Attempts to install dental implants in posterior regions of the maxillary and mandibular arches have, however, encountered several unique problems.

On the one hand, such attempts have been frustrated by the presence of the inferior alveolar mandibular canal in the posterior mandible, and by the presence of the sinus cavities superior to the posterior maxillary bone. Risk of invading the sinus cavities and the mandibular canal is generally avoided, the result being that often in these posterior regions no more than about 8 mm or less of bone depth is available in which to bore a site to receive a dental implant fixture. Therefore, very short implants were placed with fewer cubic millimeters in bone for foundation. Lekholm reported reduced success with shorter implants. (2nd Int. Tissue International Congress, Rochester, Minnesota, Sept. 1990). In order to place longer implants in these regions, many surgeons have resorted to more different techniques, including sinus lift procedures and mandibular canal repositioning. These procedures are obviously of greater risk than standard implant treatment in the anterior regions of the mouth. It is an advantage of the present invention to avoid these procedures. Some practitioners have sought to overcome this problem in the mandible, if the mandibular canal is located in a buccal position, by installing an available dental implant fixture closer to the lingual surface, and thereby bypassing the mandibular canal, when adequate bone is available to the lingual surface to avoid the risk of fenestration. This procedure, when available, may have the advantage of providing partial primary stabilization in cortical bone, which is important for eventual osseointegration of the fixture with the bone.

It has become apparent that wider jawbones (as in the posterior regions) usually have less trabeculation and often are without adequate amounts of density of bone in their marrow spaces to provide anchorage for dental implants. In the maxillary and mandibular posterior regions the bone is cancellous internally and cortical externally, a condition sometimes termed "eggshell". It has been found to be often almost impossible to securely immobilize a dental implant in the marrow spaces of posterior jawbone regions. Jaffin & Berman noted less success in bone in posterior regions. J. Periodontal, 1991, 62:2–4. It has been suggested that the only hope of more predictable success in these cases is to place a dental implant so as to engage a denser, more cortical layer of bone that often protects the maxillary and nasal sinuses, or that covers the mandibular canal, or engaging buccal-lingual plates in the posterior mandible or maxilla, all of which have inherent surgical risk.

The above-described difficulties and proposed solutions are presented in greater detail in an article by Langer, B. et al entitled "Osseointegration: Its impact on the Interrelationships of Periodontics and Restorative Dentistry: Part 1: The International Journal of Periodontics & Restorative Dentistry, Volume 9, Number 2, 1989, at pages 85 to 105.

GENERAL NATURE OF THE INVENTION

In accordance with the present invention a dental implant having a cylindrically-shaped post portion which is preferably not more than about 10 mm long has a diameter large enough (about 5 or 6 mm) to make bone-to-implant contact with cortical bone at both the lingual and buccal sides of posterior "eggshell" jawbone without coming into contact with either the mandibular canal or the sinus floor. This new implant has several advantages:

a - it has a length-to-width ratio in a range from about 0.833 to about 2.0 in dimensions providing bilateral bone-to-implant contact, without making contact with the mandibular canal or the sinus floor;

b - by contacting cortical bone at both sides of the bore in the jawbone it provides more complete initial stabilization to the installed dental implant fixture; Langer et al., at page 89, show an installation in which a standard prior-existing long thin implant fixture is located to engage lingual cortical plate to provide initial stabilization, which obviously does not provide this advantage; the installation is in an unfavorable position for the construction of a fixed prosthesis;

c - owing to its larger width it provides a more stable platform for molar restorations than is available from the prior existing narrower implant fixtures, as well as larger surface area of an implant contact with bone, which results in smaller actual stresses in the bone-implant interface under a given occlusal load; these advantage are also lacking in Langer et al. Although the reaction of bone to stresses imposed by occlusal loading on implant fixtures is not well known and understood, it appears reasonable that any loading in the posterior regions of the mouth where cancellous bone is prevalent would benefit from a wider distribution of these stresses in the cortical bone because of the ability of the wider implant to engage both cortices.

d - non-circular (e.g.: hexagonal) manipulative and non-rotational devices now in use can be made wider to improve manipulation of the fixture and stabilization of restorations, especially single-tooth crowns, supported on them. In the existing state of the art with dental implant, the ratio of the width of the non-rotating feature to the total diameter of the implant is in a range of approximately 0.7 to 0.8 mm. Maintaining this same ratio in a larger diameter implant (5 or 6 mm in diameter, for example) obviously makes it possible to utilize a much larger dimension in the non-rotational features of the implant.

This larger dimension when used in conjunction with prosthetic components that have similar clearances or fit allowances between them as currently exist in the state of the art, provides for a much more stable interlocking mechanism. Essentially this revolves around the concept of retaining a minimum gap or fit between two components, but increasing the relative sizes of both of these components. By doing so, one allows the state of the art in existing manufacturing to be easily utilized to accomplish a more stable restoration when utilizing a larger diameter in the non-rotational dimensions of the components. By way of simple illustration, if one imagines a one-thousandth of an inch gap between an abutment and an implant fixture given the current state of the art, there will be a certain amount of play or micro movement between the prosthetic components and the implant fixture. If one can double the size of the non-rotational fitting, while still maintaining the same one-thousandth of an inch gap, the relative amount of motion or micro-movement between the prosthetic components and the implant fixture will decrease accordingly. The reduction of this relative motion is of significant advantage in keeping prosthetic components tight, particularly when used in single tooth applications.

In addition to the advantages offered by increased width of nonrotating fittings, the opportunity to increase the height or depth of such fittings may also offer significant advantages, particularly in single tooth restorations. The stability of the screw joint complex in single tooth restorations in the molar region is more important than in other regions of the mouth because of increased occlusal loads in this area. The addition of wider non-rotating features and taller or deeper non-rotating features, such as higher hexes or deeper hex sockets, will increase the integrity of the screw joint complex thereby reducing problems associated with micro movement and screw loosening.

e - Its larger size has advantages with regard to the final restoration and tooth emergence profile. Particularly in the posterior regions of the mouth where molars may be replaced, a larger diameter emergence profile may be desirable. This is particularly true in single tooth applications where it is important to preserve the emergence profile of a natural tooth in order to maintain subgingival contours which are easily cleaned and do not function as traps for debris and food. To create such tooth emergence profiles with smaller diameter implant fixtures often requires procedures such as ridge lapping or lingual bulking of restorative materials which makes hygiene very difficult. In anterior regions of the mouth it is often possible to overcome the shortcomings of narrower diameter implants by placing the implant more apically in the restored ridge. This allows for gradual contouring of the restoration subgingivally and can result in a more natural tooth emergence profile. However, in the posterior regions of the mouth this is often not practical because of limitations in anatomy which have been mentioned previously.

These and other advantages and features of the invention will become apparent from the following description of exemplary embodiments of the invention with reference to the accompanying drawings.

DETAILED DESCRIPTION OF THE DRAWINGS

Figure 1:
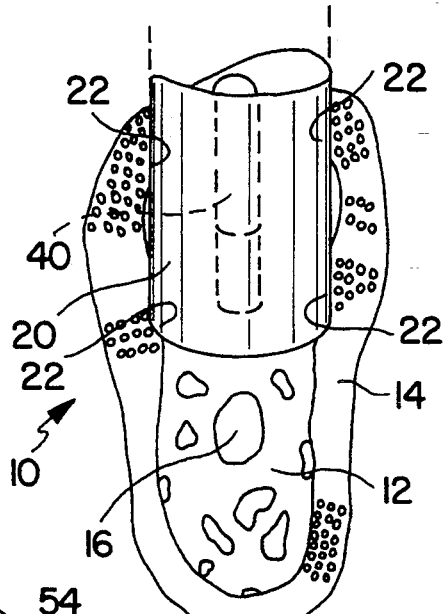
FIG. 1 is a schematic view of the cross-section of a mandibular posterior region with a dental implant fixture of the invention installed.

FIG. 1 represents a posterior region 10 of a mandible, showing a typical eggshell configuration which is cancellous internally 12 and cortical externally 14. The mandibular canal 16 is in the cancellous portion of the mandible. A dental implant 20 (shown more completely in FIG. 2) is installed in the mandible making partial bone-to-implant contact with the lingual and buccal cortical walls 14 at locations labelled 22. For the most part, the implant displaces cancellous bone 12. The bone-to-implant contacts 22 provide near-total initial stabilization to the implant at both the lingual and the buccal sides of the mandible.

Figure 1A:
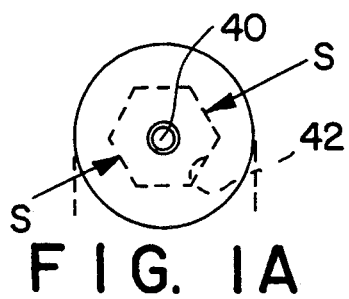
FIG. 1A is a schematic top view of FIG. 1.
Figure 2:
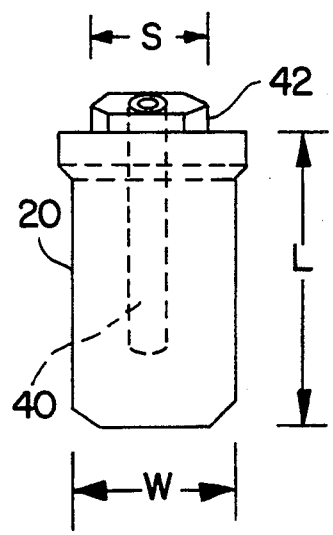
FIG. 2 illustrates features of dental implant fixtures according to the invention.

Referring now to FIG. 2, the implants of this invention has length L and width W dimensions which are unique and unlike the dimension of typical implants that are in regular current use. The ratio L/W is a range from about 0.833 to about 2.00. For example, L may be not more than 8 to 10 mm, while W may be up to about 7 or 8 mm, depending on the width of the jawbone at the posterior location chosen for the implant. The limit on L is dictated by the location of the mandibular canal 16, which may be less than 8 or 10 mm In contrast to these unusual dimensions, implants currently available have lengths up to about 20 mm, and widths up to 4 mm, thus having L/W ratios as high as 4.5, for example. A dental implant having this L/W ratio and limited to L not greater than about 8 to 10 mm would not be able to make bone-to-implant contact with both sides of the cortical shell in a mandibular location.

Figure 3:
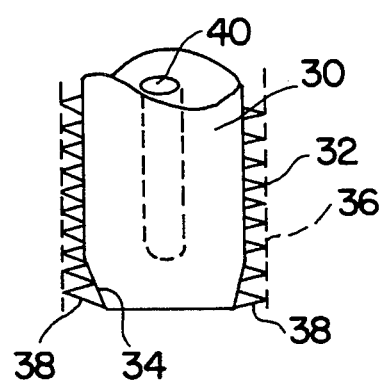
FIG. 3 is a partial side view of an externally-threaded implant fixture.

FIG. 3 shows an implant 30 bearing screw threads 32 on its outer surface. In accordance with this embodiment the lower portion 34 of the implant body is tapered to a smaller diameter than the major portion of the implant body, but the peaks of the threads 32 are on a fixed cylindrical locus 36, so that the lower few threads 38 are deeper than all the others. This feature may be used when desired, in implants according to the present invention to provide deeper penetration of the threads into the cortical bone well within the jawbone and thereby enhance primary stabilization of the implant in the cortical bone.

Figure 4A:
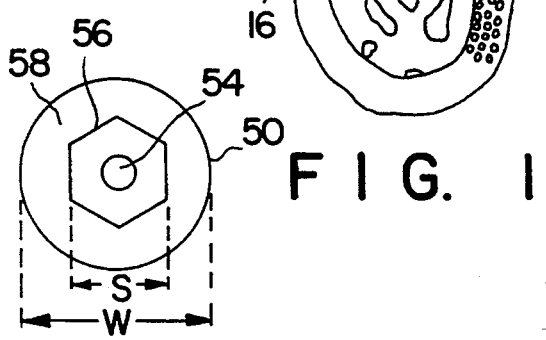
FIG. 4A is a top view of FIG. 4.
Figure 4:
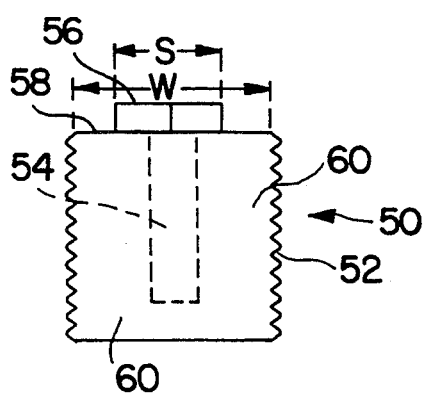
FIG. 4 is a side view of another externally-threaded fixture.

FIGS. 4 and 4A show an implant 50 bearing exterior screw threads 52 on a cylindrical body 60 of substantially uniform diameter.

Figure 5:
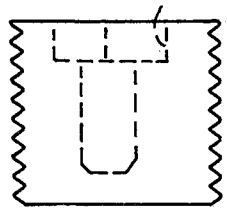
FIG. 5 is a side view of still another dental implant fixture.

In common with prior existing implants, the implants of this invention may have a receiving bore 40 (in FIGS. 2 & 3; 54 in FIGS. 4 & 4A) for receiving and holding restoration components (not shown). This bore may be internally threaded as shown at 54 in FIG. 4. A non-circular (e.g: hexagonal) fitting 42 (FIG. 2), 56 (on top surface 58 in FIG. 4), may be provided, externally as shown in these figures, or internally 66 as shown in FIG. 5 for the known purposes of manipulation the implant and for stabilizing a restoration component against rotation with respect to the implant, around their common axis. The distance S between two opposite flat surfaces of this fitting may, however, be larger in the present invention than in the prior known implants, and the ratio between the width W and the dimension S can be selected to provide enhanced stabilization to the restoration components and to the restoration built on them, as is explained above in this specification.

Thus, for example, S can be greater than the usual 3 mm, while W can be up to about 10 mm. A dimension of S at 4 mm is closer to the diameter of a posterior tooth, and therefore more stabilizing. This yields a ratio of W/S that is 2.5. If S is still larger, this ratio becomes smaller.

We claim:

1. A method of installing a dental implant in a posterior region of a living human jawbone where said jawbone is cancellous internally and cortical externally and is characterized by lingual and buccal cortical plates bounding a relatively large mass of cancellous bone occupying a major portion of the buccal-to-lingual thickness of said jawbone, comprising the steps of preparing an implant receiving bore in said jawbone at a selected site ins aid region, the diameter of said bore being large enough to reach both of said plates, stopping said bore short of the mandibular canal or the maxillary sinus, as the case may be, choosing an implant having a diameter W at least as large as the diameter of said bore and a length L not larger than the depth of said bore, and installing said implant in said bore so as to make bone-to-implant contact with each of said plates and thereby to effect initial stabilization of said implant in said bore.

2. A method according to claim 1 including the step of preparing said bore to a diameter greater than 5 mm.

3. A method according to claim 1 including the step of preparing said bore to a depth greater than 5 mm but not greater than about 10 mm.

4. A method according to claim 1 including the step of preparing said bore to a diameter not greater than about 8 mm.

5. A method according to claim 1 including the step of preparing said bore to a diameter greater than about 5 mm, and a depth not greater than about 10 mm.

6. A method according to claim 1 in which said implant fixture is chosen to have a length-to-width ratio, L/W which is in a range from less than one-to-one to not more that about than two-to-two.

* * * * *

UNITED STATES PATENT AND TRADEMARK OFFICE
CERTIFICATE OF CORRECTION

PATENT NO. : 5,364,268

DATED : 11/15/94

INVENTOR(S) : Richard J. Lazzara et al

It is certified that error appears in the above-indentified patent and that said Letters Patent is hereby corrected as shown below:

Claim 1, col. 5, line 21: change "ins aid" to --in said--.

Claim 6, col. 6, line 20, delete "fixture"; and
line 22, change "two-to-two" to --two-to-one--.

Signed and Sealed this

Seventh Day of March, 1995

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,364,268
DATED : November 15, 1994
INVENTOR(S) : Richard J. Lazzara et al It is certified that error appears in the above-indentified patent and that said Letters Patent is hereby corrected as shown below:

On the title page, item [54] and in column 1, line 3, in the title please delete "FIXTURE".

In item [57] Abstract, line 3, delete "ant" and insert --and--.

Claim 1, col. 5, line 21, change "ins aid" to --in said--.

Claim 6, col. 6, line 20, delete "fixture" and
          line 22, change "two-to-two" to --two-to-one--.

This certificate supersedes certificate of correction issued on March 7, 1995.

Signed and Sealed this

Fifth Day of March, 1996

*Attest:*

BRUCE LEHMAN

*Attesting Officer*     *Commissioner of Patents and Trademarks*